United States Patent [19]
Howard

[11] Patent Number: 4,926,876
[45] Date of Patent: May 22, 1990

[54] DIAGNOSIS OF MUSCLE PROBLEMS

[76] Inventor: John M. H. Howard, 100 Crabtree Lane, Harpenden, Herts AL5 5RF, England

[21] Appl. No.: 264,624

[22] Filed: Oct. 31, 1988

[51] Int. Cl.[5] .............................................. A61B 5/00
[52] U.S. Cl. ................................................... 128/736
[58] Field of Search ........................................ 128/736

[56] References Cited

U.S. PATENT DOCUMENTS

| | | | |
|---|---|---|---|
| 2,888,918 | 6/1959 | Pierce et al. | 128/736 |
| 4,218,707 | 8/1980 | Reed et al. | 128/736 |
| 4,347,854 | 9/1982 | Gosline et al. | 128/736 |
| 4,428,382 | 1/1984 | Walsall et al. | 128/736 |
| 4,494,550 | 1/1985 | Blazek et al. | 128/736 |

FOREIGN PATENT DOCUMENTS

| | | | |
|---|---|---|---|
| 692175 | 10/1930 | France | 128/736 |
| 1120966 | 10/1984 | U.S.S.R. | 128/736 |
| 80/1514 | 7/1980 | World Int. Prop. O. | 128/736 |

Primary Examiner—Kyle L. Howell
Assistant Examiner—John C. Hanley
Attorney, Agent, or Firm—Parmelee, Bollinger & Bramblett

[57] ABSTRACT

A process for diagnosing suspected muscle problems in a subject, comprises observing the difference in temperature between opposite limbs of the subject while one is at rest and the other is exercised. Analysis of the, say, plot of the difference allows a physician to assess immediately whether the subject is, for example, magnesium-deficient, and to prescribe accordingly.

10 Claims, 5 Drawing Sheets

NORMAL MYOTHERMOGRAM

MILD MAGNESIUM DEFICIENCY

RESTING

MILD MAGNESIUM DEFICIENCY

MILD ISOMETRIC EXCERCISE

MILD MAGNESIUM DEFICIENCY

MILD MECHANICAL EXCERCISE

SEVERE MAGNESIUM DEFICIENCY 90  80  70  60

RESTING

SEVERE MAGNESIUM DEFICIENCY 90  80  70  60  50

MILD ISOMETRIC EXERCISE

SEVERE MAGNESIUM DEFICIENCY 90  80  70  60

MILD MECHANICAL EXERCISE

MAGNESIUM REPLETION 90  80  70  60

1 MONTH

MAGNESIUM REPLETION 90  80  70

2 MONTHS

MAGNESIUM REPLETION 90  80  70  60

3 MONTHS

Fig. 5A
Fig. 5B
CALCIUM DEFICIENCY
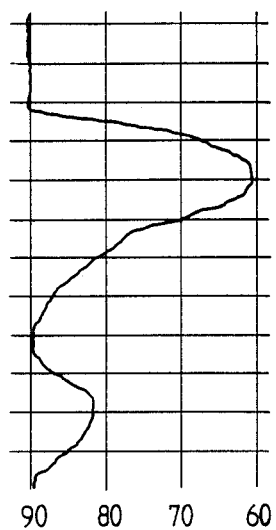
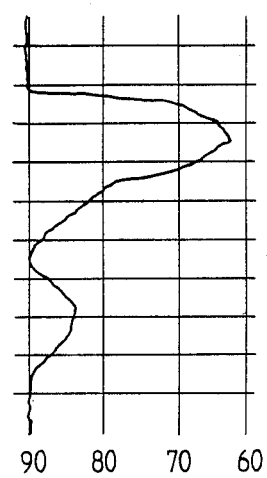
90  80  70  60     90  80  70  60
<u>THE SAME PATIENT</u>
TESTS 2 DAYS APART
Fig. 6
IRON DEFICIENCY
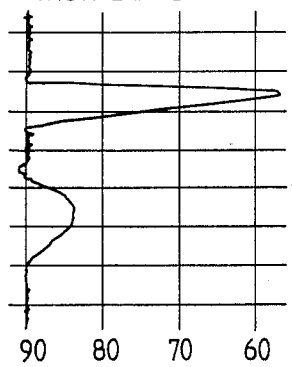
90  80  70  60
(7 YEAR OLD CHILD)
Fig. 7
HYPOTHYROIDISM
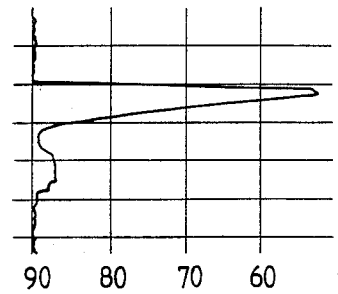
90  80  70  60

HYPERTHYROIDISM

PYREXIA (39·3°C)

FEMALE (AGE 30)

FOLATE DEFICIENCY

MALE (AGE 46)

SEVERE MAGNESIUM DEFICIENCY WITH MUSCLE DAMAGE

DIAGNOSIS OF MUSCLE PROBLEMS

FIELD OF THE INVENTION

This invention relates to the diagnosis of muscle problems.

BACKGROUND OF THE INVENTION

In the investigation of muscle problems, it is relatively easy to measure the circulating levels of nutrients known to be involved in muscle function. Such data frequently fail to provide enough information about metabolic problems within the muscle. In diagnosis, and in following the treatment of muscle-related problems, a functional test is needed.

A helpful description of the theoretical and physiological aspects of muscle function is given by Poland et al (1981) The Musculoskeletal System, 2nd Edn., pp. 8-73, London: Henry Kimpton.

SUMMARY OF THE INVENTION

This invention is based on use of the fact that, in the sub-cellular events responsible for muscle contraction, the biochemical energy utilised must equal the energy output of the system, and this is essentially the external work done plus the heat energy produced. The external work can be limited so that a plot of the heat produced during contraction and relaxation should reflect the sub-cellular chemistry. The limiting factors are the difficulty of detecting very small temperature changes and the efficient way in which muscle heat is conducted away by the circulation, but the test is considerably more efficient and direct than the measurement of circulating nutrients whose levels may be affected by many factors other than those affecting the levels in the muscles.

A process of this invention, for diagnosing suspected muscle problems in a subject, comprises observing the difference in temperature between opposite limbs of the subject while one limb is at rest and the other is exercised.

DESCRIPTION OF THE DRAWINGS

Each of FIGS. 1 to 11 is a plot (hereinafter described as a "myothermogram") from a pen-chart recorder, of recorded differential heat from a patient, against time.

DESCRIPTION OF THE INVENTION

The temperature of each limb is measured directly by a detector. For example, integrated circuit transducers are used to detect the changes in temperature. The output of each device increases by, say, 10 mV per 1° C. increase in temperature. Two detectors are employed and the difference between their outputs is processed and recorded. The result is suitably provided for observation on a standard pen-chart recorder.

One detector is placed over an upper arm muscle at rest. The other detector is placed in the mirror image position on the other arm which is then subjected to movement or to a range of muscle movements. There are no electrical connections with the patient. The detector surface indents the skin by about 2 to 3 mm. Simple switching arrangements allow the selection of differential mode or separate channel recording. An operational amplifier circuit provides additional amplification and low or high pass filters for the examination of fine details.

A chart speed of 120 mm per minute is used in routine testing. Higher speeds are sometimes of value in the investigation of muscle tremor situations. To assist in patient-to-patient comparisons, the sensitivity may be adjusted to give a single contraction peak height of, say, about 80 mm on the recorder chart.

In use, the resting heat base-line is recorded until there is an absence of drift, which usually takes between 2 and 15 minutes. The recording is continued during a simple arm movement which contracts the muscle, and this arm position is maintained until the recording is stable. The patient then returns the arm to the resting position and the recording is continued until the base-line is once again stable.

The recording is repeated after very mild isometric exercise and again after mild mechanical exercise. In normal control subjects, the three traces are almost identical. The principal features of a normal myothermogram are shown in FIG. 1.

Figure 1:
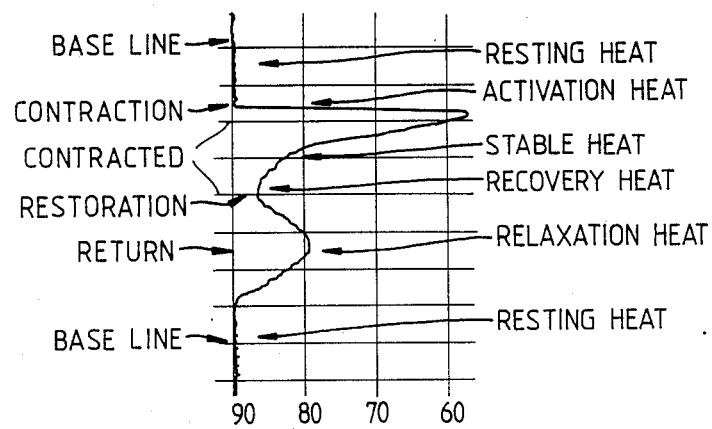

With reference to FIG. 1, the "resting heat" is that given off under basal conditions. There is no voluntary mechanical movement involved. The arm is comfortably at rest. Resting heat is from oxidative processes, and quickly falls if the circulation is restricted.

The "initial heat" is produced during a contraction. There is a burst of "activation heat" which parallels changes in intracellular calcium, followed by the "stable heat" from ATP hydrolysis (cross-bridge movement). The stable heat is proportional to tension and hence the number of cross-bridges in operation.

"Recovery heat" is given off slowly following a contraction. It reflects oxidative processes restoring the muscle to its pre-contraction biochemical state. It in additional to the resting heat. This part of the trace is altered in a dramatic way when circulatory efficiency is reduced.

"Relaxation heat" is produced when the muscle is stretched to its pre-contracted length. Increased external work is required to achieve this stretching in magnesium deficiency, some thyroid disorders, calcium disturbance and in pyrexia. These increase relaxation heat.

In magnesium deficiency, an erratic base-line is found. Quite frequently, there are signs of muscle tremor after mild exercise. The resting heat and the relaxation heat are increased. The stable heat is increased. The leading edge of the contraction peak remains normal (which, as will be seen, is not so in calcium or folate deficiencies).

Figure 2A:
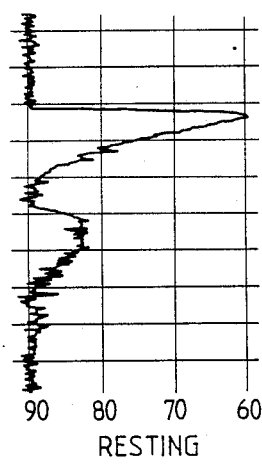
Figure 2B:
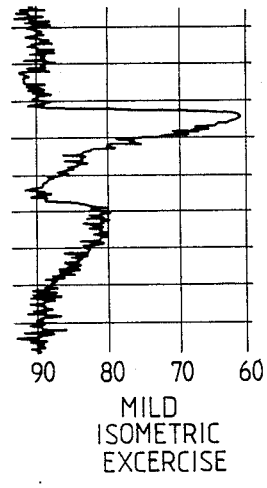
Figure 2C:
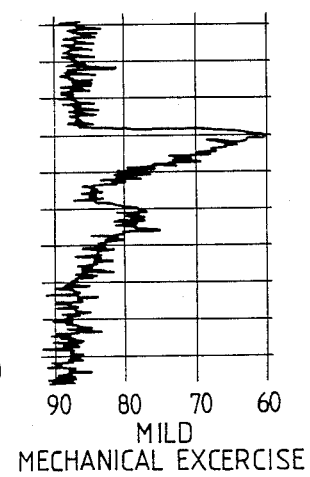

FIGS. 2A, 2B and 2C are typical of mild magnesium deficiency. FIGS. 3, 3B and 3C demonstrate the very high level of disturbance seen in severe magnesium deficiency.

Figure 3A:
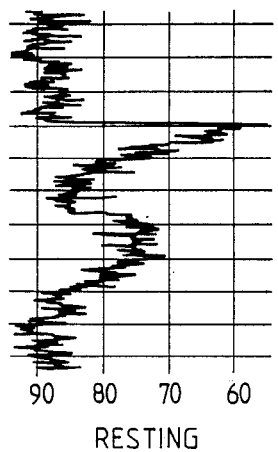
Figure 3B:
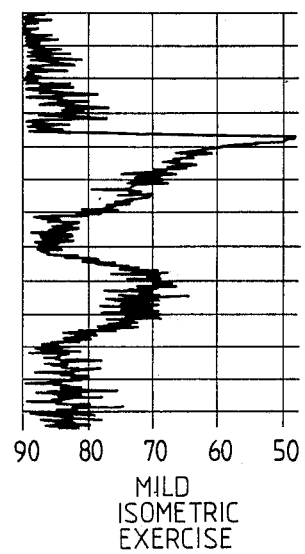
Figure 3C:
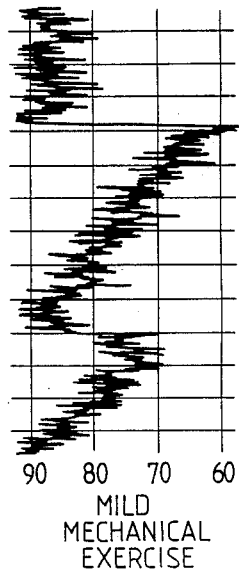

In the case shown in FIGS. 3A-3C, there was a clinically obvious muscle tremor after mild exercise. The widening of the contraction peak is due to an early shift from oxygen to glucose use and demonstrates poor oxygenation or perfusion of the tissue. This represents a very useful diagnostic feature of the novel test.

Figure 4A:
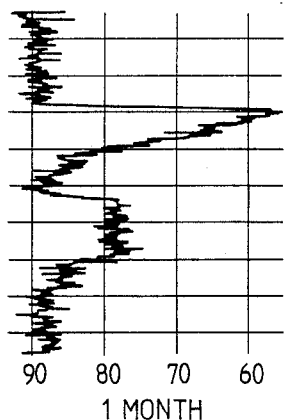
Figure 4B:
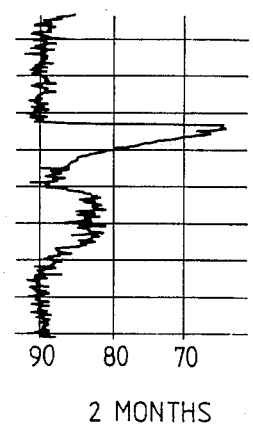
Figure 4C:
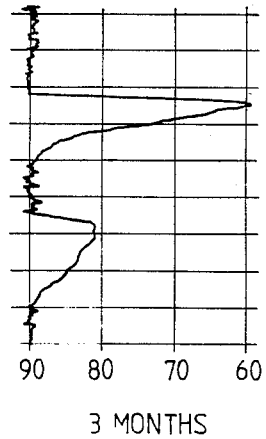

FIGS. 4, 4B and 4C are the test results obtained at various stages of magnesium repletion of the patient represented in FIGS. 3A-3C.

In calcium deficiency, the rise time is prolonged, and heat production continues to exceed the cooling efficiency of the circulation for some seconds after the muscle movement ceases. The base-line is very stable and there is a marked increase in stable heat. See FIGS. 5A and 5B.

Iron deficiency has a marked effect on the test in children. The stable heat is absent, which presumably reflects changes in the cytochrome cascade which is iron-dependent. The effect is not nearly so marked in iron-deficient adults. FIG. 6 shows the pattern obtained from an iron-deficient 7-year old girl who had reduced serum iron and ferritin levels and an increased transferrin level.

In four teenaged patients without vascular problems or magnesium deficiency, the widening of the contraction peak that is seen in reduced oxygenation or perfusion was found. These patients had low serum manganese levels. All four were given manganese supplements. In all cases the test results normalised within four weeks and three of the four had complete correction of the clinical muscle problem. The fourth had only about 50% improvement.

Patients taking lithium compounds have decreased resting heat and stable heat. There is also a tendency towards base-line drift. Some organic drugs, including barbiturates, have effects on the recovery heat and the relaxation heat.

Decreased resting heat, stable heat, recovery heat and relaxation heat are seen in hypothyroidism. This is shown in FIG. 7.

Figure 8:
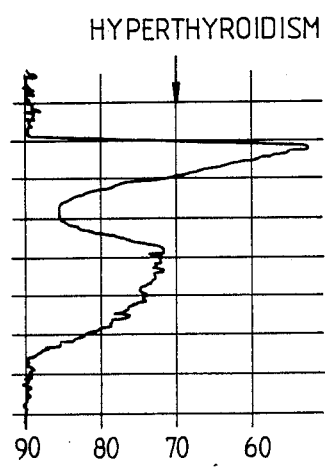
Figure 9:
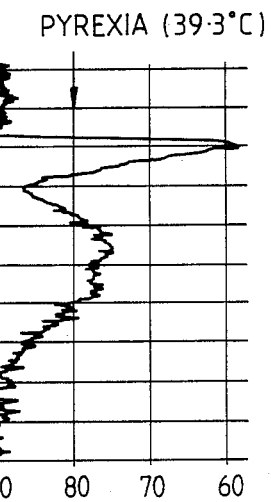

Hyperthyroidism and pyrexia lead so similar changes in the test results, as shown in FIGS. 8 and 9.

Figure 10A:
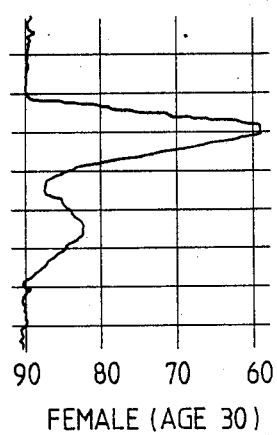
Figure 10B:
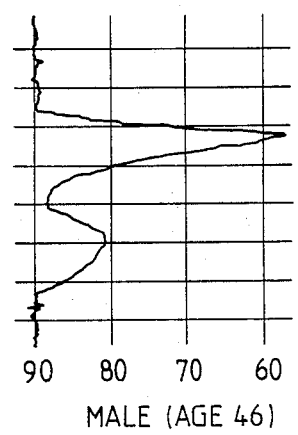

In folate deficiency, the changes seen include an erratic contraction peak, as demonstrated in FIG. 10.

In lacticacidosis, the changes are those that have already been mentioned in relation to reduced oxygenation and perfusion.

Figure 11:
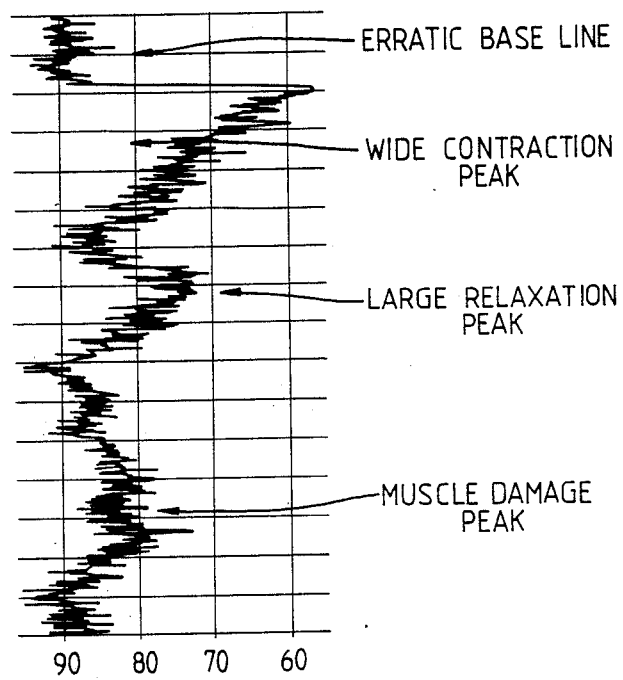

In marked magnesium deficiency, an extra peak may be seen in the test pattern. This occurs when relaxation is so seriously inhibited that accessory muscles are used to pull apart the cross-bridging. This muscle damage can occur at very low exercise levels. The muscle damage peak is demonstrated in FIG. 11.

The novel test is therefore useful in relating clinical muscle problems to the sub-cellular events responsible for contraction and relaxation. The test has diagnostic value in helping to identify deficiencies of essential nutrients and it provides secondary information about perfusion and oxygenation. A physician who is familiar with the possible patterns can very quickly assess a likely cause of the patient's problem, and prescribe an effective antidote, e.g. a dietary regime in which a nutrient such as magnesium is increased.

I claim:

1. A process for diagnosing suspected muscle problems in a subject, which comprises measuring the difference in temperature between opposite limbs of the subject while one limb is at rest and the other is exercised determining said difference as a function of time, and diagnosing muscle problems from the determined function.

2. A process according to claim 1, wherein said difference as a function of time is compared directly or indirectly with a corresponding temperature difference as a function of time obtained from a control (healthy) person.

3. A process according to claim 1, wherein said exercise comprises one or more of normal muscle contraction, isometric exercise and mechanical exercise.

4. A process according to claim 1, wherein said exercise is performed after ensuring that there is absence of drift in said measured temperature difference .

5. A process according to claim 1, wherein said muscle problem is diagnosed as being associated with deficiency of a nutrient selected from magnesium, calcium, manganese and folate.

6. A process according to claim 5, which comprises the subsequent step of repletion of said nutrient.

7. A process according to claim 1, wherein said muscle problem is diagnosed as being associated with a condition selected from hypothyroidism, hyperthyroidism and pyrexia.

8. A process according to claim 7, which comprises the subsequent step of administering to said subject a regime intended to counteract said condition.

9. A process according to claim 1, wherein said muscle problem is diagnosed as being associated with a condition selected from poor oxygenation and poor perfusion of the tissue, hypothyroidism, hyperthyroidism and pyrexia.

10. A process according to claim 9, which comprises the subsequent step of treating the subject to counteract said condition.

* * * * *